United States Patent
Culver et al.

(10) Patent No.: US 9,277,898 B2
(45) Date of Patent: Mar. 8, 2016

(54) STATIONARY ANTERIOR PHASED ARRAY COIL FOR SIMULTANEOUS PET-MR IMAGING

(71) Applicant: General Electric Company, Schenectady, NY (US)

(72) Inventors: Craig William Culver, Neosho, WI (US); John Edward Lorbiecki, Hubertus, WI (US); Bijay Kamleshbhai Shah, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 477 days.

(21) Appl. No.: 13/728,384

(22) Filed: Dec. 27, 2012

(65) Prior Publication Data
US 2014/0187910 A1    Jul. 3, 2014

(51) Int. Cl.
| | |
|---|---|
| *A61B 5/05* | (2006.01) |
| *A61B 6/00* | (2006.01) |
| *A61B 5/00* | (2006.01) |
| *A61B 6/03* | (2006.01) |
| *A61B 5/055* | (2006.01) |

(52) U.S. Cl.
CPC ............. *A61B 6/4417* (2013.01); *A61B 5/0035* (2013.01); *A61B 6/037* (2013.01); *A61B 5/055* (2013.01)

(58) Field of Classification Search
CPC .... A61B 6/4417; A61B 6/037; A61B 5/0035; A61B 5/055
USPC ......................................................... 600/411
See application file for complete search history.

(56) References Cited

U.S. PATENT DOCUMENTS

| | | | |
|---|---|---|---|
| 2,975,825 A * | 3/1961 | Gedris et al. ..................... 297/41 |
| 6,433,549 B1 | 8/2002 | Dean et al. | |
| 7,382,132 B1 | 6/2008 | Mathew et al. | |
| 7,386,338 B2 | 6/2008 | Hoppel et al. | |
| 7,449,888 B1 | 11/2008 | Malik et al. | |
| 2005/0077896 A1* | 4/2005 | Angelos et al. ............... 324/309 |
| 2006/0052685 A1* | 3/2006 | Cho et al. ....................... 600/407 |
| 2008/0164875 A1* | 7/2008 | Haworth et al. .............. 324/318 |
| 2009/0308400 A1* | 12/2009 | Wilson et al. .................. 128/845 |
| 2013/0218000 A1* | 8/2013 | Coppens et al. .............. 600/411 |

OTHER PUBLICATIONS

Goel et al., Seismic strengthening of an RC slab-column frames with ductile steel bracing, paper No. 506, Eleventh World Conference on Earthquake Engineering, 1996.*
Stabilizer Bar Kits, http://ipscorp.com/plumbing/watertite/pipesupports/stabilizerkits, Imaging captured by wayback machine, Oct. 26, 2012.*

* cited by examiner

*Primary Examiner* — Bo J Peng

(57) ABSTRACT

A PET-MR apparatus includes an MR imaging system for acquiring MR signals and a PET system for acquiring PET emissions of the patient. The PET-MR apparatus also includes an anterior surface coil configured to receive MR signals from a volume-of-interest of the patient in the bore and resulting from the emitted RF pulse sequence and a coil positioning structure mounted to the PET-MR apparatus and configured to receive the anterior surface coil thereon and position the anterior surface coil proximate to the volume-of-interest of the patient without coming in contact with the patient, with the coil positioning structure being configured to provide both a vertical adjustment of the anterior surface coil relative to a coronal plane of the patient and an angular adjustment of the anterior surface coil relative to the coronal plane of the patient.

20 Claims, 4 Drawing Sheets

STATIONARY ANTERIOR PHASED ARRAY COIL FOR SIMULTANEOUS PET-MR IMAGING

BACKGROUND OF THE INVENTION

Embodiments of the invention relate generally to positron emission tomography (PET) and magnetic resonance (MR) imaging, and more specifically, to a combined PET-MR system incorporating a stationary anterior phased array surface coil that can be positioned stationary relative to a patient or patient table, with the coil being constructed so as to enable isolation of the coil from the patient and so as to minimize any affect on PET-MR image acquisition.

PET imaging involves the creation of tomographic images of positron emitting radionuclides in a subject of interest. A radionuclide-labeled agent is administered to a subject positioned within a detector ring. As the radionuclides decay, positively charged photons known as "positrons" are emitted therefrom. As these positrons travel through the tissues of the subject, they lose kinetic energy and ultimately collide with an electron, resulting in mutual annihilation. The positron annihilation results in a pair of oppositely-directed gamma rays being emitted at approximately 511 keV.

It is these gamma rays that are detected by the scintillators of the detector ring. When struck by a gamma ray, each scintillator illuminates, activating a photovoltaic component, such as a photodiode. The signals from the photovoltaics are processed as incidences of gamma rays. When two gamma rays strike oppositely positioned scintillators at approximately the same time, a coincidence is registered. Data sorting units process the coincidences to determine which are true coincidence events and sort out data representing deadtimes and single gamma ray detections. The coincidence events are binned and integrated to form frames of PET data which may be reconstructed into images depicting the distribution of the radionuclide-labeled agent and/or metabolites thereof in the subject.

MR imaging involves the use of magnetic fields and excitation pulses to detect the free induction decay of nuclei having net spins. When a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

In MRI, it is desirable for the excitation and reception to be spatially uniform in the imaging volume for better image uniformity. In a standard MRI system, the best excitation field homogeneity is usually obtained by using a whole-body volume RF coil for transmission. The whole-body transmit coil is the largest RF coil in the system. A large coil, however, produces lower signal-to-noise ratio (SNR) if it is also used for reception, mainly because of its greater distance from the signal-generating tissues being imaged. Because a high signal-to-noise ratio is the most desirable in MRI, "surface coils" are commonly employed for reception to enhance the SNR from a particular volume-of-interest. Such surface coils are relatively small and are constructed to receive the MR signal from a localized portion of the patient. For example, different surface coils may be employed for imaging the head and neck, legs and arms, or various internal organs. One particular type of surface coil that is often employed is an anterior array surface coil that is used to image a region-of-interest located in an anterior portion (i.e., a frontal portion) of the patient.

Currently, the industry standard is to place the anterior array surface coil on top of the patient, such that it rests on the patient. As a result, this surface coil moves as the patient breaths or moves. However, this movement of the surface coil creates a number of challenges with regards to a PET-MR hybrid system, namely because the positioning of ancillary devices on the patient (e.g., surface coils) has never been a requirement for PET imaging since conventional PET imaging systems eliminate all random-placed accessories relative to the patient to reduce artifact. In employing a surface coil for acquiring MR image data during a PET-MR imaging acquisition, the motion of the surface coil makes the attenuation correction process challenging, as there would be a need to know the position of surface coil real-time during imaging. And while patient motion correction is not new to either PET or MR, the combination of the two imaging modalities in one simultaneous process creates completely unique challenges. Namely, conventional "patient breath-holds" or special MR scan sequences that are often employed for stand-alone MR imaging will not be adequate for PET-MR imaging.

It would therefore be desirable to provide a surface coil for use in a PET-MR system that can be positioned stationary relative to a patient or patient table, such that movement of the coil that might be caused by patient movement is eliminated. It would also be desirable for the surface coil to have a construction that minimizes any affect on PET-MR image acquisition, such as by forming the surface coil from a material having a low proton density and material density.

BRIEF DESCRIPTION OF THE INVENTION

Embodiments of the invention provide a combined PET-MR system incorporating a system for positioning an anterior surface coil array in a stationary position relative to a patient or patient table.

In accordance with one aspect of the invention, a PET-MR apparatus includes a magnetic resonance (MR) imaging system having a plurality of gradient coils positioned about a bore of a magnet, and an RF coil assembly coupled to a pulse generator to emit an RF pulse sequence for use in acquiring MR signals from a patient in the bore. The PET-MR apparatus also includes a positron emission tomography (PET) system having a detector array positioned around a PET tube encircling the bore, with the detector array being controlled to acquire PET emissions of the patient. The PET-MR apparatus further includes an anterior surface coil configured to receive MR signals from a volume-of-interest of the patient in the bore and resulting from the emitted RF pulse sequence and a coil positioning structure mounted to the PET-MR apparatus and configured to receive the anterior surface coil thereon and position the anterior surface coil proximate to the volume-of-interest of the patient without coming in contact with the patient, with the coil positioning structure being configured to provide both a vertical adjustment of the anterior surface coil relative to a coronal plane of the patient and an angular adjustment of the anterior surface coil relative to the coronal plane of the patient.

In accordance with another aspect of the invention, a PET-MR apparatus includes a magnetic resonance imaging (MRI) system configured to acquire MR signals from a patient, the MRI system having a plurality of gradient coils positioned about a bore of a magnet and an RF coil assembly coupled to a pulse generator to emit an RF pulse sequence. The PET-MR apparatus also includes a positron emission tomography (PET) system integrated into the MRI system and having a PET detector positioned on a PET tube encircling the bore, with the PET detector being controlled to acquire PET emissions of the patient. The PET-MR apparatus further includes an anterior surface coil comprising one or more coil elements that is configured to receive MR signals from a volume-of-interest of the patient in the bore resulting from the emitted RF pulse sequence and a coil positioning structure having the anterior surface coil retained thereon, the coil positioning structure being configured to position the anterior surface coil relative to the volume-of-interest and maintain the anterior surface coil in an isolated position from the patient so as to not be in contact with the patient, such that the anterior surface coil is not affected by patient movement or system vibration of the PET-MR apparatus. The coil positioning structure is composed of one or more materials configured to minimize attenuation of the acquired MR signals and PET emissions.

In accordance with yet another aspect of the invention, an anterior surface coil positioning structure for use in a combination PET-MR imaging system includes a coil framework configured to hold an array of anterior surface coil elements in a predetermined shape, a pair of mounting brackets configured to affix the coil positioning structure to the PET-MR imaging system, and a pair of tracks joined to the mounting brackets. The anterior surface coil positioning structure also includes sliding members retained within the tracks and being movable along the track in a vertical direction, so as to enable adjustment of the coronal position of the anterior surface coil relative to a patient, and a hinge system joining the coil framework to the sliding members, the hinge system configured to enable angular adjustment of the coil framework relative to the coronal plane, while maintaining the coil framework perpendicular to a sagital plane.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

An anterior surface coil array positioning system for use in a PET-MR system is provided. The anterior surface coil array positioning system enables vertical adjustment of the coronal positioning of the anterior surface coil array relative to a patient as well as angular adjustment of the anterior surface coil array relative to the coronal plane, such that the coil array can be bridged or cantilevered over a patient that is to be imaged while still isolating the anterior surface coil array from the patient.

Figure 1:
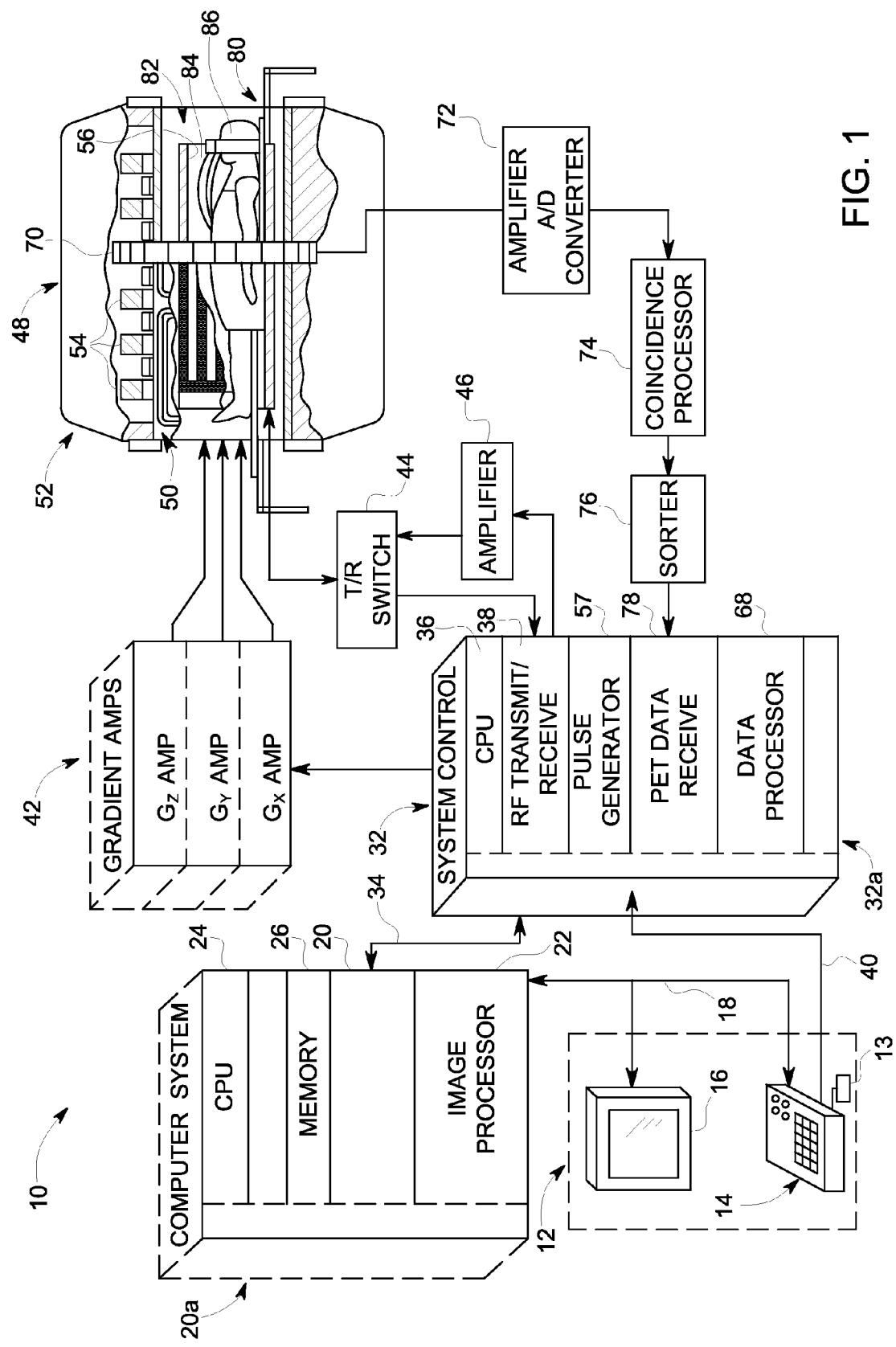
FIG. 1 is a schematic block diagram of an exemplary PET-MR imaging system for use with an embodiment of the invention.

Referring to FIG. 1, the major components of an exemplary hybrid PET-MR imaging system 10 that may incorporate embodiments of the present invention are shown. The operation of the system may be controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules, such as an image processor module 22, a CPU module 24 and a memory module 26. The computer system 20 may also be connected to permanent or back-up memory storage, a network, or may communicate with a separate system control 32 through link 34. The input device 13 can include a mouse, keyboard, track ball, touch activated screen, light wand, or any similar or equivalent input device, and may be used for interactive geometry prescription.

The system control 32 includes a set of modules in communication with one another and connected to the operator console 12 through link 40. It is through link 34 that the system control 32 receives commands to indicate the scan sequence or sequences that are to be performed. For MR data acquisition, an RF transmit/receive module 38 commands the scanner 48 to carry out the desired scan sequence, by sending instructions, commands, and/or requests describing the timing, strength and shape of the RF pulses and pulse sequences to be produced, to correspond to the timing and length of the data acquisition window. In this regard, a transmit/receive switch 44 controls the flow of data via amplifier 46 to scanner 48 from RF transmit module 38 and from scanner 48 to RF receive module 38. The system control 32 also connects to a set of gradient amplifiers 42, to indicate the timing and shape of the gradient pulses that are produced during the scan.

The gradient waveform instructions produced by system control 32 are sent to the gradient amplifier system 42 having Gx, Gy, and Gz amplifiers. Amplifiers 42 may be external of scanner 48 or system control 32, or may be integrated therein. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and an RF coil assembly 56. Alternatively, the gradient coils of gradient coil assembly 50 may be independent of the magnet assembly 52. RF coil assembly may include a whole-body RF transmit coil 56 as shown. The coils 56 of the RF coil assembly may be configured for both transmitting and receiving, or for transmit-only or receive-only. A pulse generator 57 may be integrated into system control 32 as shown, or may be integrated into scanner equipment 48, to produce pulse sequences or pulse sequence signals for the gradient amplifiers 42 and/or the RF coil assembly 56. In addition, pulse generator 57 may generate PET data blanking signals synchronously with the production of the pulse sequences. These blanking signals may be generated on separate logic lines for subsequent data processing. The MR signals resulting from the excitation pulses, emitted by the excited nuclei in the patient, may be sensed by the whole body coil 56 and are then transmitted to the RF transmit/receive module 38 via T/R switch 44. The MR signals are demodulated, filtered, and digitized in the data processing section 68 of the system control 32.

An MR scan is complete when one or more sets of raw k-space data has been acquired in the data processor 68. This raw k-space data is reconstructed in data processor 68 which operates to transform the data (through Fourier or other techniques) into image data. This image data is conveyed through link 34 to the computer system 20 where it is stored in memory 26. Alternatively, in some systems computer system 20 may assume the image data reconstruction and other functions of data processor 68. In response to commands received from the operator console 12, the image data stored in memory 26 may be archived in long term storage or may be further processed by the image processor 22 or CPU 24 and conveyed to the operator console 12 and presented on the display 16.

In combined MR-PET scanning systems, PET data may be acquired simultaneously with the MR data acquisition described above. Thus, scanner 48 also contains a positron emission detector array or ring 70, configured to detect gamma rays from positron annihilations emitted from a subject. Detector array 70 preferably includes a plurality of scintillators and photovoltaics arranged about a gantry. Detector array 70 may, however, be of any suitable construction for acquiring PET data. In addition, the scintillator packs, photovoltaics, and other electronics of the detector array 70 need not be shielded from the magnetic fields and/or RF fields applied by the MR components 54, 56. However, it is contemplated that embodiments of the present invention may include such shielding as known in the art, or may be combined with various other shielding techniques.

Gamma ray incidences detected by detector array 70 are transformed, by the photovoltaics of the detector array 70, into electrical signals and are conditioned by a series of front-end electronics 72. These conditioning circuits 72 may include various amplifiers, filters, and analog-to-digital converters. The digital signals output by front end electronics 72 are then processed by a coincidence processor 74 to match gamma ray detections as potential coincidence events. When two gamma rays strike detectors approximately opposite one another, it is possible, absent the interactions of random noise and signal gamma ray detections, that a positron annihilation took place somewhere along the line between the detectors. Thus, the coincidences determined by coincidence processor 74 are sorted into true coincidence events and are ultimately integrated by data sorter 76. The coincidence event data, or PET data, from sorter 76 is received by the system control 32 at a PET data receive port 78 and stored in memory 26 for subsequent processing 68. PET images may then be reconstructed by image processor 22 and may be combined with MR images to produce hybrid structural and metabolic or functional images. Conditioning circuits 72, coincidence processor 74 and sorter 76 may each be external of scanner 48 or system control 32, or may be integrated therein.

Also included in PET-MR imaging system 10 is a patient support assembly 80 configured to support the patient within the imaging system during data acquisition. The patient support assembly 80 extends into a main magnet bore 84 of the imaging system 10 and extends through the imaging system so that its length is generally parallel to the bore axis. The patient support assembly 80 enables movement of the patient into various positions with respect to the imaging system 10, including a loading position outside the bore of imaging system 10 and at least one imaging position, where at least a portion of a patient is positioned within an imaging volume (i.e., within the bore) when at the imaging position.

As further shown in FIG. 1, an anterior surface coil 84 is included in hybrid PET-MR imaging system 10 to enhance MR data acquisition from a particular volume-of-interest located in the anterior region of a patient. According to one embodiment of the invention, the anterior surface coil 84 functions as a receive coil that receives RF signals transmitted by the whole-body RF coil 56, with the anterior surface coil 84 being positioned adjacent the volume-of-interest to enhance the SNR therefrom. A coil positioning structure 86 is provided in conjunction with the anterior surface coil 84 to enable positioning of the surface coil array relative to the patient.

Figure 2:
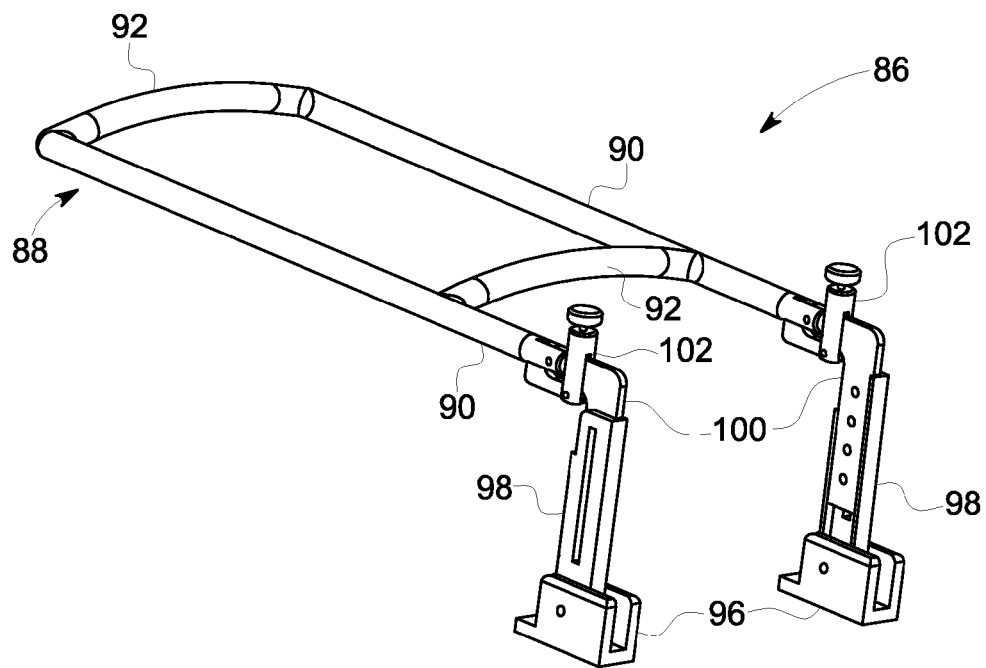
FIGS. 2 and 3 are perspective views of a coil positioning structure included in the PET-MR imaging system of FIG. 1 that is configured to support and position an anterior surface coil array relative to a patient, according to an embodiment of the invention.
Figure 3:
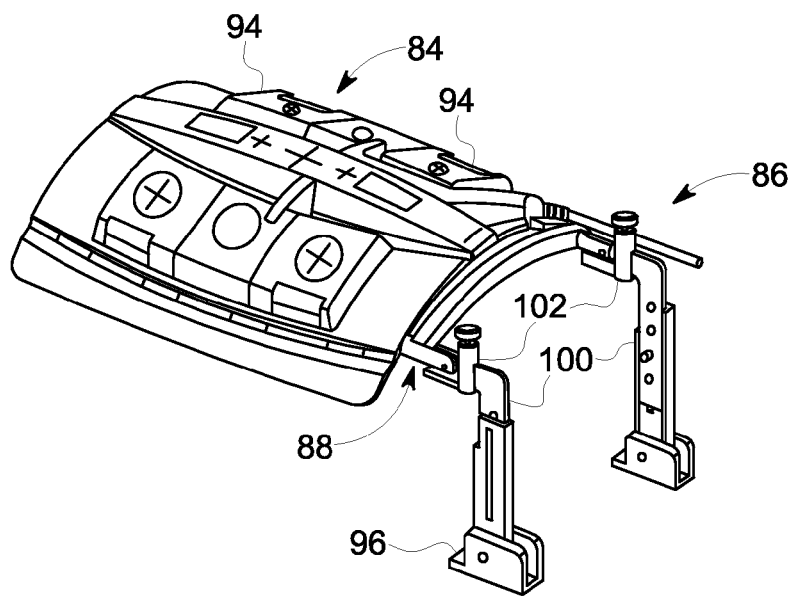

Referring now to FIGS. 2 and 3, detailed views of an exemplary coil positioning structure 86, both by itself and with the surface coil 84 included thereon, are shown according to an embodiment of the invention. The coil positioning structure includes a coil framework 88 configured to hold the surface coil 84 in a predetermined shape. As shown in the embodiment of FIG. 2, the coil framework 88 includes a pair of rod-shaped members 90 spaced apart from one another and a pair of linking members 92 that join the rod-shaped members 90 to provide structural stability and strength to the coil framework 88. As shown in FIG. 3, the surface coil 84 is formed of an array of coil elements 94 that can be used individually (switchable coil) or combined, as desired by a system operator.

Referring still to FIGS. 2 and 3, according to one embodiment of the invention, the coil framework 88 is formed separately from the anterior surface coil 84, with the coil elements 94 of the anterior surface coil 84 being positioned on the coil framework 88 to retain the general shape of the coil framework 88. According to another embodiment of the invention, the coil framework 88 is integrated within the surface coil 84, such that the coil framework 88 and the surface coil 84 are provided/formed as a single, integral component.

Also included in coil positioning structure 86 is a pair of mounting brackets 96 for securing the structure to the PET-MR imaging system 10 at a desired location, as will be explained in greater detail below. Secured to the mounting brackets 96, or formed integrally therewith, is a pair of tracks 98 configured to receive sliding members 100 therein. The sliding members 100 are movable along the tracks 98 in a vertical direction, so as to enable adjustment of the coronal orientation (i.e., up and down) of the anterior surface coil array 84 relative to a patient. The coil framework 88 is joined to the sliding members 100 by way of a hinge system 102 that provides for angular adjustment of the coil framework 88 (and the anterior surface coil array 84) relative to the coronal plane, while maintaining the coil framework 88 perpendicular to the sagital plane. The hinge system 102 is configured such that the coil framework 88 and surface coil array 84 will remain at a desired angular position until further force is applied (either manually or in an automated fashion) to move the framework to another location.

The construction of coil positioning structure 86 beneficially enables positioning of the anterior surface coil array 84 in proximity to a volume-of-interest of a patient to be imaged, as the anterior surface coil array 84 can be bridged or cantilevered over a patient that is to be imaged while still isolating the anterior surface coil array from the patient (i.e., no physical contact). The vertical adjustment of the coil framework 88 (and the anterior surface coil array 84) that is enabled by the translation of sliding members 100 within tracks 98, in conjunction with the angular adjustment of the coil framework 88 (and the anterior surface coil array 84) that is enabled by the hinge system 102, provides for positioning of the anterior surface coil array 84 proximate to such a volume-of-interest of the patient regardless of the size or girth of the patient.

According to an exemplary embodiment of the invention, the coil positioning structure 86 is formed of a material (or materials) having a very low proton density and very little material density, so to be compatible with MRI and PET imaging. That is, the coil positioning structure 86 should be formed of a material having a proton and material density as low as possible, while still meeting the mechanical structural needs of the positioning structure, such that any compensation necessary in the software processing to accommodate use of the coil positioning structure 86 and surface coil 84 is minimized. As an example, the components of coil positioning structure 86 may be composed of a Kevlar fiber reinforced epoxy, although other materials with similar proton and material densities are also recognized as being suitable for forming the coil positioning structure 86. It is further noted that the coil positioning structure 86 is also designed to have a very consistent makeup, so that PET attenuation correction can be applied successfully.

Figure 4:
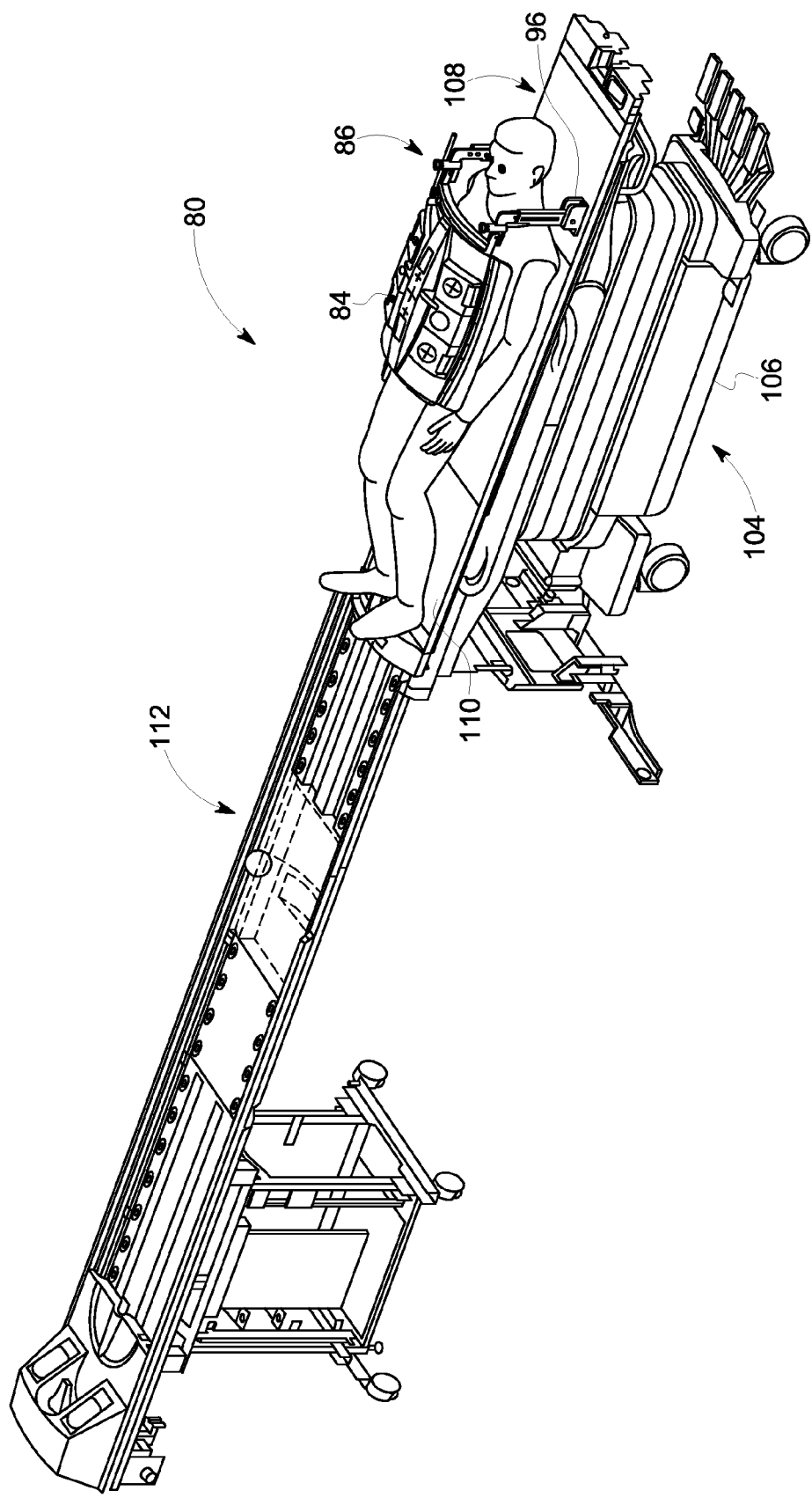
FIG. 4 is a perspective view of a patient support assembly included in the PET-MR imaging system of FIG. 1, and of the coil positioning structure mounted thereto, according to an embodiment of the invention.
Figure 5:
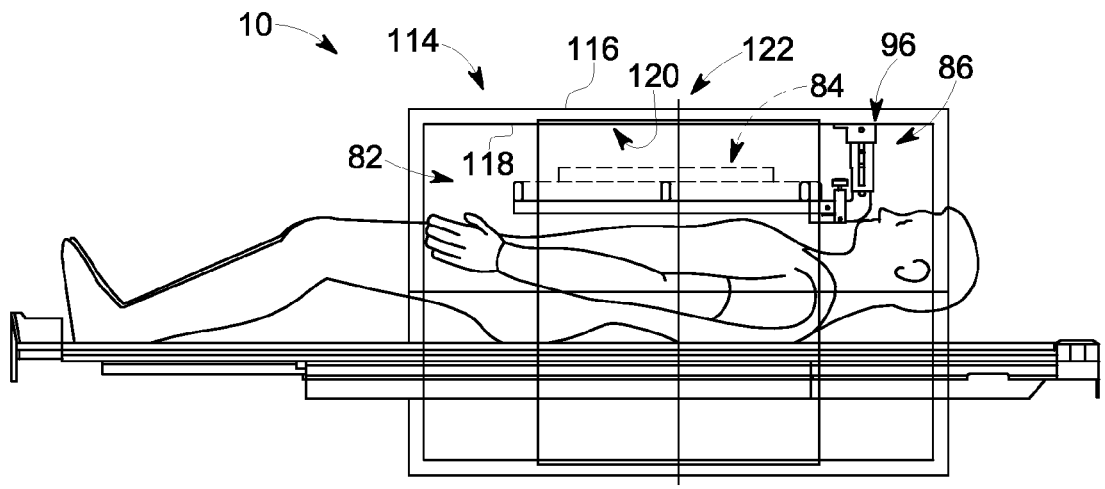
FIGS. 5 and 6 are a side view and end view, respectively, of a PET tube structure included in the PET-MR imaging system of FIG. 1, and of the coil positioning structure mounted thereto, according to an embodiment of the invention.
Figure 6:
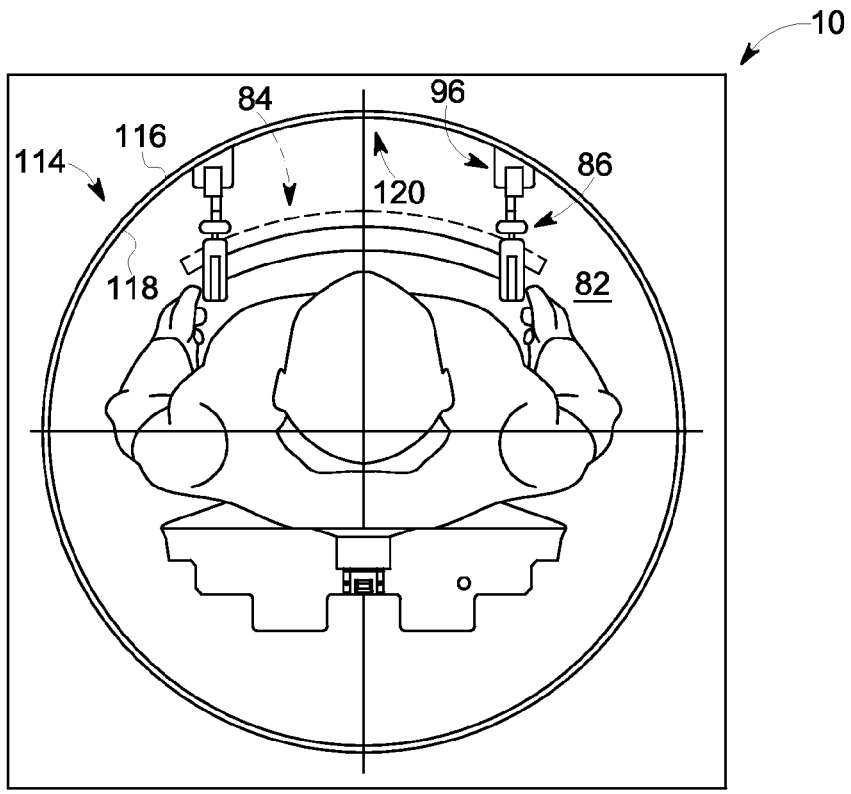

Referring now to FIGS. 4-6, a mounting of the coil positioning structure 86 within the PET-MR imaging system is shown according to varying embodiments of the invention. Referring first to FIG. 4, a mounting of the coil positioning structure 86 to the patient support assembly 80 is shown according to one embodiment of the invention. As is seen in FIG. 4, the patient support assembly 80 includes a patient bed 104 that supports the patient and provides for transport of the patient to and from the imaging system 10. The patient bed 104 includes a base structure 106 and a table 108 that is removable from the base structure 106 to enable transfer of the patient from the bed into the bore 82 (FIG. 1) of the PET-MR imaging system 10 for performing of an imaging scan. The table 88 further includes a cradle 110 that facilitates movement of the table through the imaging system 10, with the cradle 110 being translatable along a bridge assembly 112 of the patient support assembly 80 to move the patient to desired imaging locations within the imaging system 10. According to an exemplary embodiment, the cradle 110 is constructed as a thin, Kevlar cradle. The height of the patient bed 106 may be adjusted as needed in order to position the table 108 appropriately for transfer of the patient into the imaging system 10, such that the cradle 110 may slide off of the base structure 106 and into the imaging system 10.

In the embodiment shown in FIG. 4, the coil positioning structure 86 is mounted to the cradle 110, such as via mounting brackets 96 being affixed to the cradle 110, such that the anterior surface coil array 84 moves with the patient as the patient is translated through the bore 82 (FIG. 1) of the PET-MR imaging system 10. The anterior surface coil array 84 thus remains stationary relative to the patient, so as to minimize the challenges regarding image attenuation correction.

Referring now to FIGS. 5 and 6, a mounting of the coil positioning structure 86 at a fixed location within the bore 82 of the PET-MR imaging system 10 is shown according to another embodiment of the invention. In FIGS. 5 and 6, a PET tube structure 114 included in PET-MR imaging system 10 is shown, with the PET tube structure 114 including a PET tube 116 formed about bore 82. A PET tube skin 118 is also included in PET tube structure 114 and is positioned between the PET tube 116 and the patient being imaged.

The coil positioning structure 86 is mounted to the PET tube structure 114 (i.e., mounting brackets 96 are bolted to the PET tube structure 114) such that the anterior surface coil array 84 (shown in phantom) is positioned at a fixed location within the bore of the PET-MR imaging system 10, with the patient moving underneath the coil array as he/she is translated through the bore 82 of the PET-MR imaging system 10. According to one embodiment of the invention, and as shown in FIGS. 5 and 6, the coil positioning structure 86 is affixed to a top-interior surface 120 of the PET tube structure 114 and is positioned such that the surface coil 84 is aligned at the isocenter 122 of the PET-MR imaging system 10. In operation, the positioning structure 86 lowers the anterior surface coil 84 down to the patient from its attached position on the top-interior surface 120 of the tube structure, such as via mechanics like arms or straps (not shown) or via pneumatics like cylinders or bladders (not shown) that are used to push/pull the coil to the patient. If the patient/patient cradle needed to move during the scan, the surface coil 84 would be retracted upward to allow this movement, and then move back down into position proximate to the patient.

Beneficially, embodiments of the invention thus provide a coil positioning structure for use in a PET-MR system that provides for positioning of an anterior surface coil array. The coil positioning structure enables vertical adjustment of the coronal positioning of the anterior surface coil array relative to a patient as well as angular adjustment of the anterior surface coil array relative to the coronal plane, such that the coil array can be bridged or cantilevered over a patient that is to be imaged while still isolating the anterior surface coil array from the patient. The coil positioning structure is mounted within the PET-MR imaging system such that the anterior surface coil array is positioned stationary relative to a patient or patient table, so as to minimize the challenges regarding image attenuation correction. The positioning system is composed of materials that minimize any affect on PET-MR image acquisition, so to be compatible with MRI and PET imaging.

Therefore, according to one embodiment of the invention, a PET-MR apparatus includes a magnetic resonance (MR) imaging system having a plurality of gradient coils positioned about a bore of a magnet, and an RF coil assembly coupled to a pulse generator to emit an RF pulse sequence for use in acquiring MR signals from a patient in the bore. The PET-MR apparatus also includes a positron emission tomography (PET) system having a detector array positioned around a PET tube encircling the bore, with the detector array being controlled to acquire PET emissions of the patient. The PET-MR apparatus further includes an anterior surface coil configured to receive MR signals from a volume-of-interest of the patient in the bore and resulting from the emitted RF pulse sequence and a coil positioning structure mounted to the PET-MR apparatus and configured to receive the anterior surface coil thereon and position the anterior surface coil proximate to the volume-of-interest of the patient without coming in contact with the patient, with the coil positioning structure being configured to provide both a vertical adjustment of the anterior surface coil relative to a coronal plane of the patient and an angular adjustment of the anterior surface coil relative to the coronal plane of the patient.

According to another embodiment of the invention, a PET-MR apparatus includes a magnetic resonance (MR) imaging system configured to acquire MR signals from a patient, the MR system having a plurality of gradient coils positioned about a bore of a magnet and an RF coil assembly coupled to a pulse generator to emit an RF pulse sequence. The PET-MR apparatus also includes a positron emission tomography (PET) system integrated into the MRI system and having a PET detector positioned on a PET tube encircling the bore, with the PET detector being controlled to acquire PET emissions of the patient. The PET-MR apparatus further includes an anterior surface coil comprising one or more coil elements that is configured to receive MR signals from a volume-of-interest of the patient in the bore resulting from the emitted RF pulse sequence and a coil positioning structure having the anterior surface coil retained thereon, the coil positioning structure being configured to position the anterior surface coil relative to the volume-of-interest and maintain the anterior surface coil in an isolated position from the patient so as to not be in contact with the patient, such that the anterior surface coil is not affected by patient movement or system vibration of the PET-MR apparatus. The coil positioning structure is composed of one or more materials configured to minimize attenuation of the acquired MR signals and PET emissions.

According to yet another embodiment of the invention, an anterior surface coil positioning structure for use in a combination PET-MR imaging system includes a coil framework configured to hold an array of anterior surface coil elements in a predetermined shape, a pair of mounting brackets configured to affix the coil positioning structure to the PET-MR imaging system, and a pair of tracks joined to the mounting brackets. The anterior surface coil positioning structure also includes sliding members retained within the tracks and being movable along the track in a vertical direction, so as to enable adjustment of the coronal position of the anterior surface coil relative to a patient, and a hinge system joining the coil framework to the sliding members, the hinge system configured to enable angular adjustment of the coil framework relative to the coronal plane, while maintaining the coil framework perpendicular to a sagital plane.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A PET-MR apparatus comprising:
a magnetic resonance (MR) imaging system having a plurality of gradient coils positioned about a bore of a magnet, and an RF coil assembly coupled to a pulse generator to emit an RF pulse sequence for use in acquiring MR signals from a patient in the bore;
a positron emission tomography (PET) system having a detector array positioned around a PET tube encircling the bore, with the detector array being controlled to acquire PET emissions of the patient;
an anterior surface coil configured to receive MR signals from a volume-of-interest of the patient in the bore and resulting from the emitted RF pulse sequence; and
a coil positioning structure mounted to the PET-MR apparatus and configured to receive the anterior surface coil thereon and position the anterior surface coil proximate to the volume-of-interest of the patient without coming in contact with the patient, the coil positioning structure being configured to provide both a vertical adjustment of the anterior surface coil relative to a coronal plane of the patient and an angular adjustment of the anterior surface coil relative to the coronal plane of the patient.

2. The PET-MR apparatus of claim 1 wherein the coil positioning structure comprises:
a coil framework configured to hold the anterior surface coil in a predetermined shape;
a pair of mounting brackets configured to affix the coil positioning structure to the PET-MR imaging system;
a pair of tracks joined to the mounting brackets;
sliding members retained within the tracks and being movable along the track in a vertical direction, so as to enable adjustment of the coronal position of the anterior surface coil relative to the patient; and
a hinge system joining the coil framework to the sliding members, the hinge system configured to enable angular adjustment of the coil framework relative to the coronal plane, while maintaining the coil framework perpendicular to a sagital plane.

3. The PET-MR apparatus of claim 2 wherein the coil framework includes:
a pair of rod-shaped members spaced apart from one another; and
at least one linking member that joins the rod-shaped members to provide structural stability and strength to the coil framework.

4. The PET-MR apparatus of claim 1 wherein the anterior surface coil comprises an array of coil elements positioned on the coil framework.

5. The PET-MR apparatus of claim 1 further comprising a patient support assembly configured to provide for support and movement of the patient through the bore to enable acquisition of the MR signals and the PET emissions from the patient, the patient support assembly comprising:
a cradle configured to accommodate the patient; and
a bridge assembly configured to receive the cradle and provide for translation of the cradle therealong to move the patient to desired imaging locations within the PET-MR apparatus.

6. The PET-MR apparatus of claim 5 wherein the coil positioning structure is mounted to the cradle, such that the anterior surface coil retained thereon moves with the patient as the patient is moved to the desired imaging locations within the PET-MR apparatus.

7. The PET-MR apparatus of claim 1 wherein the PET system comprises a PET tube skin positioned between the PET tube and the patient, and wherein the coil positioning structure is mounted to at least one of the PET tube skin and the PET tube, such that the anterior surface coil is positioned at an isocenter of the PET system.

8. The PET-MR apparatus of claim 7 wherein the coil positioning structure is mounted to a top-interior surface of the PET tube skin or PET tube, with the coil positioning structure lowering the anterior surface coil proximate to the volume-of-interest of the patient to accommodate acquisition of the MR signals.

9. The PET-MR apparatus of claim 1 wherein the coil positioning structure is composed of a material compatible with MRI and PET imaging, the material having a proton density and a material density that minimizes PET attenuation and image processing corrections.

10. The PET-MR apparatus of claim 1 wherein the coil positioning structure is formed integrally with the anterior surface coil as a single component.

11. The PET-MR apparatus of claim 1 wherein the coil positioning structure is configured to maintain the anterior surface coil in an isolated position from the patient so as to not be in contact with the patient, such that the anterior surface coil is not affected by patient movement or system vibration of the PET-MR apparatus.

12. A PET-MR apparatus comprising:
   a magnetic resonance (MR) imaging system configured to acquire MR signals from a patient, the MR system having a plurality of gradient coils positioned about a bore of a magnet and an RF coil assembly coupled to a pulse generator to emit an RF pulse sequence;
   a positron emission tomography (PET) system integrated into the MRI system and having a PET detector positioned on a PET tube encircling the bore, with the PET detector being controlled to acquire PET emissions of the patient;
   an anterior surface coil configured to receive MR signals from a volume-of-interest of the patient in the bore resulting from the emitted RF pulse sequence, the anterior surface coil comprising one or more coil elements; and
   a coil positioning structure having the anterior surface coil retained thereon, the coil positioning structure being configured to position the anterior surface coil relative to the volume-of-interest and maintain the anterior surface coil in an isolated position from the patient so as to not be in contact with the patient, such that the anterior surface coil is not affected by patient movement or system vibration of the PET-MR apparatus;
   wherein the coil positioning structure is composed of one or more materials configured to minimize attenuation of the acquired MR signals and PET emissions.

13. The PET-MR apparatus of claim 12 wherein the coil positioning structure further comprises:
   a coil framework configured to retain the one or more coil elements of the anterior surface coil in a desired shape;
   a pair of mounting brackets configured to affix the coil positioning structure to the PET-MR imaging system;
   a pair of tracks joined to the mounting brackets;
   sliding members retained within the tracks and being movable along the track to adjust height of the anterior surface coil relative to the patient; and
   a hinge system joining the coil framework to the sliding members, the hinge system configured to enable angular rotation of the coil framework relative to the patient.

14. The PET-MR apparatus of claim 12 further comprising a patient support assembly configured to provide for support and movement of the patient through the bore to enable acquisition of the MR signals and the PET emissions from the patient, the patient support assembly including a cradle and a bridge assembly configured to provide for translation of the cradle therealong;
   wherein the coil positioning structure is affixed to the cradle such that the anterior surface coil is translated therewith as the patient is moved through the bore.

15. The PET-MR apparatus of claim 12 wherein the coil positioning structure is mounted to the PET tube such that the anterior surface coil is positioned at an isocenter of the PET system.

16. The PET-MR apparatus of claim 15 wherein the coil positioning structure is mounted to a top-interior surface of the PET tube, with the coil positioning structure lowering the anterior surface coil proximate to the volume-of-interest of the patient to accommodate acquisition of the MR signals.

17. An anterior surface coil positioning structure for use in a combination PET-MR imaging system, the anterior surface coil positioning structure comprising:
   a coil framework configured to hold an array of anterior surface coil elements in a predetermined shape;
   a pair of mounting brackets configured to affix the coil positioning structure to the PET-MR imaging system;
   a pair of tracks joined to the mounting brackets;
   sliding members retained within the tracks and being movable along the track in a vertical direction, so as to enable adjustment of the coronal position of the anterior surface coil relative to a patient; and
   a hinge system joining the coil framework to the sliding members, the hinge system configured to enable angular adjustment of the coil framework relative to the coronal plane, while maintaining the coil framework perpendicular to a sagital plane.

18. The anterior surface coil positioning structure of claim 17 wherein the array of anterior surface coil elements are retained on the coil framework so as to form an integral surface coil array-positioning system component.

19. The anterior surface coil positioning structure of claim 17 wherein the pair of mounting brackets mounts the anterior surface coil positioning structure to a patient support assembly configured to translate a patient through the PET-MR imaging system, such that the that the array of anterior surface coil elements are translated with the patient as the patient is moved through the PET-MR imaging system.

20. The anterior surface coil positioning structure of claim 17 wherein the pair of mounting brackets mounts the anterior surface coil positioning structure to a PET tube of the PET-MR imaging system, within a bore of the PET-MR imaging system, such that the array of anterior surface coil elements are positioned at an isocenter of the PET-MR imaging system.

* * * * *